United States Patent
Hardy et al.

(10) Patent No.: US 6,743,760 B1
(45) Date of Patent: Jun. 1, 2004

(54) TRANSPARENT CONDITIONING SHAMPOO

(75) Inventors: Eugene Hardy, Old Bridge, NJ (US); Anthony Psihoules, Hillsborough, NJ (US)

(73) Assignee: Colgate-Palmolive Company, NY, NY (US)

( * ) Notice: Subject to any disclaimer, the term of this patent is extended or adjusted under 35 U.S.C. 154(b) by 0 days.

(21) Appl. No.: 10/447,966

(22) Filed: May 29, 2003

(51) Int. Cl.[7] .............................. C11D 1/83; C11D 3/37
(52) U.S. Cl. .................. 510/125; 510/119; 510/122; 510/123; 510/124; 510/421; 510/422; 510/424; 510/426; 510/427; 510/466; 510/503; 510/490
(58) Field of Search ................................ 510/119, 122, 510/123, 124, 125, 421, 422, 424, 426, 427, 466, 503, 490

(56) References Cited

U.S. PATENT DOCUMENTS

| | | |
|---|---|---|
| 5,114,706 A | 5/1992 | Duvel |
| 5,166,297 A | 11/1992 | O'Lenick, Jr. |
| 5,302,322 A | 4/1994 | Birtwistle |
| 5,326,483 A | 7/1994 | Halloran et al. |
| 5,876,705 A * | 3/1999 | Uchiyama et al. ........ 424/70.12 |
| 6,194,363 B1 | 2/2001 | Murray |
| 6,495,498 B2 | 12/2002 | Niemiec et al. |

FOREIGN PATENT DOCUMENTS

| WO | WO 02/22085 | 3/2002 |
|---|---|---|

* cited by examiner

*Primary Examiner*—Charles Boyer
(74) *Attorney, Agent, or Firm*—Rosemary M. Miono

(57) ABSTRACT

A conditioning shampoo comprising:
(a) 8–18 weight % of an anionic surfactant;
(b) 0.5–0.8 weight % of a conditioning system comprising:
  (i) 0.1–0.75 weight % of silicone Quaternium-8;
  (ii) 0.1–0.5 weight % of a low molecular weight guar gum with a molecular weight less than 100,000 centipoise as an aqueous clear cationic solution of a modified polysaccharide clear cationic solution; and
  (iii) 0.1–0.5 weight % of Polyquaternium-10;
(c) 1.0–6.0 weight % of an amphoteric surfactant;
(d) 0.5–5.0 weight % of a member selected from the group consisting of cocodiethanol amide, and cocomonoethanol amide; and
(e) the remainder as water.

20 Claims, No Drawings

TRANSPARENT CONDITIONING SHAMPOO

FIELD OF THE INVENTION

This invention relates to hair cleansing and/or conditioning with the use of a selected guar gum. A clear shampoo is obtained.

BACKGROUND OF THE INVENTION

The use of silicone conditioning ingredients is frequently seen in the art and in commercial products. Such ingredients provide a high degree of both wet and dry combing ability to a variety of hair types. The use of such silicone materials requires the presence of a stabilizing agent such as ethylene glycol disteatate, C20–40 alcohols, behenyl alcohol, to name a few. While the stabilizing agents provide stability, they also add to the opaqueness of the final product. The opaqueness can be desirable if a pearlized product is desired, but it makes it impossible to achieve clear products. In addition, the use of dimethicone at typical use levels delivers unacceptable translucency and typically poor stability profiles. Further, the use of alternatives to dimethicone such as dimethicone copolyols, amodimethicone, or PEG silicone surfactants, or the exclusive use of polyquaterniums as polymeric conditioning agents can provide transparent shampoo systems but they do not provide the required beneficial conditioning properties to hair as evaluated with wet and dry combing tests.

Previous attempts at formulating hair care compositions include the following references.

U.S. Pat. No. 5,114,706 to Duvel describes hair conditioning shampoos comprising cationic dialkyl conditioning agents in combination with long chain fatty alcohols and non-volatile silicones that are suspended by cross-linked polymeric suspending agents.

U.S. Pat. No. 5,302,322 to Birtwistle describes a shampoo comprising a cationic deposition polymer, a surfactant, and a water-insoluble end-functionalized quaternary silicone polymer capable of dissolving in the surfactant.

U.S. Pat. No. 6,194,363 to Murray describes small particle size emulsified silicone in combination with amino functional silicones to boost conditioning properties of the conditioning shampoo.

U.S. Pat. No. 6,495,498 to Niemiec et al describes a 2-in-1 detergent system comprising a water soluble silicone agent, a cationic conditioning agent and a detergent.

U.S. Pat. No. 5,326,483 to Halloran et al describes a clear shampoo product which contains a cationic oil-in-water emulsion of an amine functional polydimethyl silicone and a method of making a clear and stable shampoo composition with the absence of a pearling agent.

PCT Publication WO 02/22085 describes a method for treating the hair with a transparent concentrated hair conditioning composition.

BRIEF SUMMARY OF THE INVENTION

This invention relates to the use of a selected quaternized silicone conditioning agent in combination with a selected guar gum and Polyquaternium-10. The quaternized silicone is recognized under the INCI designation-silicone Quaternium-8 (tradename Ultrasil Q-8 and Ultrasil Q8 Plus), both from Noveon, Inc. Cleveland Ohio. All three ingredients are necessary for forming products according to the invention. The omission of the guar gum reduces wet comb-ability and poorer lathering properties while also reducing the viscosity of the final product. The omission of the silicone quaternary materials reduces dry comb-ability and there is less of a smooth feel to washed hair. Omission of the Polyquaternium-10 reduces formulation viscosity and foam slip and results in a less desirable coated feel to the hair. If the level of cationic guar gum is raised to improve the lesser desired properties without Polyquaternium-10, the formulation becomes slightly hazy. Thus, all the ingredients listed above are critical to the formulation of an acceptable product.

DETAILED DESCRIPTION OF THE INVENTION

The conditioning shampoos of the invention comprise:
  (a) 8–18 weight % (particularly 8–12%) of an anionic surfactant;
  (b) 0.5–0.8 weight % of a conditioning system comprising:
    (i) 0.1–0.75 weight % (particularly 0.3–0.6% and, more particularly, 0.5%) of a silicone quaternium material which is silicone Quaternium-8 (INCI designation) (tradename Ultrasil Q-8 and Ultrasil Q8Plus);
    (ii) 0.1–0.5 weight % (particularly 0.15–0.3%) of a low molecular weight (less than 100,000 centipoise, more particularly in the range 40,000–65,000 cps) guar gum as an aqueous clear cationic solution of modified polysaccharide (such as AquaCat™ CG-518 clear cationic solution from Hercules Inc., Wilmington, Del.); and
    (iii) 0.1–0.5 weight % (particularly 0.15–0.3%) of Polyquaternium-10 (also sometimes referred to as Polymer JR);
  (c) 1.0–6.0 weight % (particularly 3–5%) of an amphoteric surfactant;
  (d) 0.5–5.0 weight % (particularly 1–3%) of a member selected from the group consisting of cocodiethanol amide ("CDEA") and cocomonoethanol amide ("CMEA") (useful as foam stabilizer and/or rheology modifier); and
  (e) the remainder as water;
provided that if CDEA is used with betaine, a salt such as NaCl or an equivalent or similar salt (such as, for example, ammonium chloride) is included in an amount of 0.1%–2.00 weight % to thicken the product to 3,500 cps or greater if a liquid non-aerosol product is to be formed. Viscosity is typically measured using a Brookfield RVT viscometer using spindle #4 and 20 r.p.m. with the sample being equilibrated to 25C.

The hair care composition of the invention comprises at least one surfactant which may be selected from anionic, nonionic, amphoteric and zwitterionic surfactants and mixtures thereof. Examples of required surfactants include at least 8 weight % of an anionic surfactant, and at least one of the following: 1) at least 0.1 weight % (particularly 1–2 weight %) amphoteric or semipolar surfactant or 2) at least 0.5 weight % (particularly 1–2 weight %) of a nonionic surfactant.

Optionally other ingredients may be included such as other types of surfactants (zwitterionic, semi-polar, nonionic) rheology modifiers, coloring agents, UV absorbers, protein derivatives, fragrance ($\leq 0.1$ weight %), and vitamins ($\leq 0.1$ weight %), may be added provided that clarity is maintained.

The clarity of the final product may be ascertained by being able to read 12 pitch typed print through a clear bottle approximately 4–5 cm (about 1.5–1.75 inches) thick using naked eye evaluation.

The conditioning shampoos of this invention are also unique since they are transparent to clear even with the use of guar gum as described above. The use of the type of guar gum as described above is important to the invention. It should also be noted that the formulations of this invention are able to achieve the required clarity without the use of microsponges. Finally, the present compositions do not require the presence of stabilizers. Thus, the formulations of this invention can (i) include silicone-free microsponges or (2) be both microsponge-free and stabilizer-free; or (3) include stabilizers not principally as stabilizers but to control foam aesthetics (add creaminess, slip, etc.).

The products of this invention may be used as liquids, placed in a pressurized container with a propellant added, or used in a pump spray form. The viscosity of the product will be selected to accommodate the form desired with a liquid having a modified viscosity in the range of 500–3000 centipoise, a non-aerosol pump spray having a viscosity in the range of –300–2000 centipoise, and an aerosol foam using a liquid material having a viscosity in the range of 300–2500 centipoise.

The low molecular weight quaternized guar gum comprising guar hydroxypropyltrimonium chloride was obtained from Hercules under the tradename—Aquacat™ CG518. For this product generally, the weight average molecular weight is between 5,000 and an upper limit of 200,000 and the light transmittance is greater than 80% at a wavelength of 600 nm in a 10% aqueous solution. Both the chemical description and method for manufacture are described in detail in U.S. patent application Ser. No. 10/139,858 filed May 6, 2002.

The water soluble silicone quaternary compound ingredient is commercially available from Noveon Inc. of Cleveland, Ohio under the tradename of Ultrasil Plus and is described in U.S. Pat. No. 5,166,297. The preferred material has an average charge density of 0.35 meq/g and is supplied as a 100% active water soluble ingredient that is prepared by the reaction of a hydroxyl containing silicone polymer with a quaternized alkylamido dimethylamine. It is a cationic silicone quat that confers to the INCI designation Silicone Quaternium-8.

The hair care invention also includes a specific cationic deposition polymer which is a cationic cellulose derivative. Suitable cationic cellulose derivatives include Polymer JR series, from Union Carbide.

Suitable anionic surfactants include the alkyl sulfates, alkyl ether sulfates, alkaryl sulfonates, alkyl sulfosuccinates, n-alkyl sarcosinates, alkyl phosphates, alkyl ether phosphates, alkyl ether carboxylates and alpha-olefin sulfonates, especially their ammonium, sodium, magnesium and mono-, di- and triethanolamine salts. The alkyl groups generally contain from 8 to 18 carbon atoms and may be saturated or unsaturated. The alkyl ether sulfates, alkyl ether phosphates and alkyl ether carboxylates may contain from 1 to 10 ethylene oxide units per molecule. One particular group of anionic surfactants are members selected from the group consisting of sodium lauryl sulfate, sodium laureth sulfate, ammonium lauryl sulfate, ammonium laureth sulfate, disodium laureth sulfosuccinate; disodium ricinoleamido monoethanolamide ("MEA") sulfosuccinate, sodium cocoyl isethionate, sodium methyl oleoyl taurate, sodium methyl cocoyl taurate, sodium laureth-13 carboxylate, sodium C14–16 olefin sulfonate, sodium laureth-4 phosphate, laureth-3 phosphate, triethylanolamine lauryl sulfate, magnesium lauryl sulfate, sodium tridecyl sulfate, and alpha-olefin sulfate. Another specific group includes ammonium laureth sulfate, ammonium lauryl sulfosuccinate and triethanolamine lauryl sulfate. The most preferred anionic surfactants are ammonium lauryl sulfate and sodium lauryl ether sulfate. The most preferred anionic surfactants are sodium lauryl sulfate, triethanolamine lauryl sulfate, sodium lauryl ether sulfate 1 EO, 2EO and 3EO and ammonium lauryl ether sulfate 1EO, 2EO and 3EO.

Suitable amphoteric surfactants are those selected from the group consisting of sultaines (such as cocamidopropyl hydroxy sultaine); glycinates (such as cocoamphocarboxyglycinates); glycines (such as cocoamidopropyldimethylglycine); propionates (such as sodium lauriminodipropionate, sodium cocamphopropionate, disodium cocoamphodipropionate, and cocoamphocarboxypropionate). In addition, Psuedo amphoteric (ampholytic) surfactants such as betaines are also commonly grouped within the designation-Amphoteric surfactants and can be used for similar purposes. Useful betaines include cocamidopropyl, coco, and oleamidopropyl.

Nonionic surfactants suitable for use in the composition of the invention may include condensation products of aliphatic (C8–18) primary or secondary linear branched chain alcohols with alkylene oxides or phenols with alkylene oxides, usually ethylene oxide and generally having from 6 to 30 ethylene oxide groups. Nonionic surfactants suitable for use in the compositions of the present invention can include fatty acid alkanolamides. Representative fatty acid alkanolamides include those having C10–C18 carbons. For example, fatty acid diethanolamides such as isostearic acid diethanolamide and coconut fatty acid diethanolamide. Suitable fatty acid monoethanolamides which may be used include coconut fatty acid monoethanolamide and coco mono-isopropanolamide. A particularly suitable nonionic surfactant includes cocodiethanolamide sold under the tradename Standamid KD from Cognis Company.

Semi-polar surfactant surfactants such as amine oxides are also suitable for use in the present invention. These include N-alkyl amine oxide, and N-stearyl dimethylamine oxide. A suitable N-acyl amide oxide includes N-cocamidopropyl dimethylamine oxide. The hydrophobic portion of the amine oxide surfactant may be provided by a fatty hydrocarbon chain having from about 10–21 carbon atoms.

While not required as a stabilizer in the invention, thickeners can be used to facilitate the application of the shampoo composition to the hair, and are preferably added in sufficient quantities to provide a more luxurious effect. Representative thickening agents which may be used are cellulose derivatives and acrylates copolymers.

A special group of thickeners useful in the invention are nonionic thickeners such as condensation products of aliphatic (C8–18) primary or secondary linear or branched chain alcohols or phenols with alkylene oxides, oxyethylcellulose, hydroxypropyl cellulose, starch and starch derivatives such as hydroxyethylamylose and starch amylase, locust bean gum bean, sodium and ammonium chloride, saccharides such as fructose and glucose and derivatives of polysaccharides such as PET-120 methyl glucose dioleate. A particularly suitable thickener is acrylates copolymer sold under the tradename AQUA SF-1 by Noveon Inc. of Brecksville, Ohio-USA.

Additional conditioners, may be added to the shampoo composition in the form of organic cationic conditioning agents for the purpose of providing more hair grooming if deemed necessary such as cationic conditioning agents that may include homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages and copolymers of vinylpyrrolidone and acrylic acid esters with quaternary nitrogen functionality. Specific materials include Polyquaterniums 7 and, 11 Other possible candidates include Polyquaterniums 8 and 23 provided that clarity can be maintained.

Cationic anti-static agents that may have some surfactant character such as cetyl trimethylammonium chloride, cetyl trimethylammonium bromide and stearyltrimethylammonium chloride may also be employed if deemed advantageous as additional cationic antistatic conditioning agents. Also included in this category are salts of primary fatty amines. The alkyl groups of such amines preferably have from about 12 to 22 carbons atoms and may be substituted or unsubstituted. Suitable amine salts include phosphate, citrate lactate and alkyl sulfate salts used at less than 1% in the formulation and should not interfere with the clarity of the final formulation.

The hair care compositions of the invention will be optically clear. However, opaque or pearlized formulations in accordance with the invention may be made by the specific addition of a pearlizing agent to the clear formula. Such agents include those known in the industry to provide a pearlizing appearance such as glycol stearate (preferably added in a vehicle to allow for the addition of a liquid such as Euperlan PK4000 from Cognis Corp.) or ethylene glycol distearate.

The hair care compositions of the invention may contain other components in minor amounts (for example less than 1%) commonly found in standard shampoo formulations such as antibacterial agents, antidandruff agents such as zinc pyridinethione, pearlizing agents, perfumes, dyes, coloring agents, preservatives, viscosity modifiers, proteins, polymers, buffering agents, polyols and other moisturizing ingredients, plant extracts, herb extracts, marine extracts and the like. The minor amounts should not interfere with the clarity.

In a further aspect of the present invention there is provided a method for preparing the hair care shampoo compositions defined below.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for molecular weights are averages. Temperatures are in degrees C unless otherwise indicated. The amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7th ed. 1997).

General Example

Formation of shampoo—Charge deionized water to a kettle of suitable size and begin mixing. Add acrylates copolymer to main mixing kettle until completely dispersed. Add anionic surfactant and mix until dispersed, clear and uniform composition is obtained. Add NaOH or other neutralizing agent to the main kettle, and mix until the composition is completely clear and batch appears noticeably thicker and uniform. Add water-soluble silicone quaternary ingredient to surfactant/water phase and mix until clear and uniform. In a separate vessel combine the quaternized cellulosic conditioning polymer with additional deionized water equal to or greater than 10 times the quantity of the polymer and mix until the polymer is dispersed. The dispersed polymer is then added to the main mixing kettle with moderate agitation until the mixture appears clear and uniform. Add the amphoteric, semipolar or ampholytic surfactant to main mixing kettle with moderate agitation until the composition is clear and uniform. Add the low molecular weight quaternized guar gum (AquaCat™ CG518 clear cationic solution) to the main mixing kettle and mix until completely dispersed and uniform. In a separate vessel, combine the nonionic surfactant with fragrance (if used) and mix until the composition is clear and homogeneous. If other water insoluble ingredients are used in the formula they are also added to the nonionic surfactant phase. Fragrance may also be added directly to the batch if desired. Add the separate mixtures to the main kettle and mix until the composition is clear and homogeneous. Add preservatives, extract and color as desired and any other water soluble ingredients used at low use levels to the main mixing kettle with moderate agitation to prevent heavy aeration of batch until the composition is clear and uniform. If desired, additional ingredients such as citric acid may be added to the main kettle to allow for pH adjustment such as to decrease the pH of the final formulation solution to a desired range. Typical batch sizes prepared in the laboratory are between 1 and 5 kilograms.

Use of shampoo—Use of the hair care shampoo composition entails the wetting of the hair, adding shampoo to the hair typically approaching 5 grams of product that is massaged onto the hair fibers and scalp to generate a dense lather. The hair is then rinsed until the foam is removed. The process may be repeated if deemed appropriate.

Examples 1–3

The following hair conditioning shampoo compositions were prepared according to the method described above in the General Example. All formulas were found to be optically clear with the exception of Example 3 to which is added a separate pearlizing agent as listed in Part 5 of that Example. Note that Example 3 also uses multiple surfactants.

Example 1

| Component | Weight % |
| --- | --- |
| Part 1 | |
| Deionized water | q.s. |
| Sodium phosphate monobasic | 0.100 |
| Acrylates copolymer (Aqua SF-1) | 1.500 |
| Ammonium lauryl sulfate-28% | 28.571 |
| NaOH (50% solution) | 0.280 |
| Cocamidopropyl betaine (30%) | 6.000 |
| Silicone Quaternium-8 (100% AI) | 0.500 |
| Part 2 | |
| Deionized water | 15.00 |
| Polyquaternium-10 (100% AI) | 0.150 |

-continued

| Component | Weight % |
|---|---|
| Part 3 | |
| Deionized water | 10.00 |
| Tetrasodium EDTA-62% | 0.120 |
| Part 4 | |
| Guar hydroxylpropyltrimonium chloride (AquaCat ™ CG518 (18% AI) from Hercules) | 0.150 |
| Part 5 | |
| Cocodiethanolamide-90% | 1.300 |
| Fragrance | 0.400 |
| Benzophenone-3 | 0.100 |
| Part 6 | |
| Color solution (0.1%) | 0.500 |
| Formalin | 0.100 |
| Water soluble Extract | 0.150 |
| Citric acid (50% solution) | 0.200 |

Example 2

| Component | Weight % |
|---|---|
| Part 1 | |
| Deionized water | q.s. |
| Sodium phosphate monobasic | 0.100 |
| Acrylates copolymer (Aqua SF-1) | 3.000 |
| Ammonium lauryl sulfate | 28.571 |
| Ammonium laureth (2EO) sulfate-25% | 8.000 |
| NaOH (50% solution) | 0.280 |
| Silicone Quaternium-8 (Ultrasil Q-Plus-100% AI) | 0.500 |
| Part 2 | |
| Deionized water | 15.00 |
| Polyquaternium-10 | 0.150 |
| Part 3 | |
| Deionized water | 10.00 |
| Tetrasodium EDTA-62% | 0.120 |
| Part 4 | |
| Guar hydroxylpropyltrimonium chloride (AquaCat ™-CG518 (18% AI)) | 0.833 |
| Part 5 | |
| Cocodiethanolamide-90% | 1.300 |
| Fragrance | 0.400 |
| Benzophenone-3 | 0.100 |
| Part 6 | |
| Color solution (0.1%) | 0.500 |
| DMDM Hydantoin | 0.450 |
| Kathon CG | 0.070 |
| Water soluble Extract | 0.100 |
| NaCl | 0.250 |
| Citric acid (50% solution) | 0.250 |

Example 3

| Component | Weight % |
|---|---|
| Deionized water | q.s. |
| Sodium phosphate monobasic | 0.100 |
| -Sodium lauryl ether (2EO) sulfate (28%) | 35.715 |
| NaOH solution (50%) | 0.280 |

-continued

| Component | Weight % |
|---|---|
| Cocamidopropyl betaine (30%) | 6.000 |
| Silicone Quaternium-8 (Ultrasil Q-Plus-100% AI) | 0.700 |
| Part 2 | |
| Deionized water | 15.00 |
| Polyquaternium-10 (100% AI) | 0.150 |
| Part 3 | |
| Deionized water | 10.00 |
| Tetrasodium EDTA-62% | 0.120 |
| Part 5 | |
| Glycol distearate (and) Laureth-4 (and) cocamidopropyl betaine (Euperlan PK4000 from Cognis) | 2.000 |
| Part 6 | |
| Guar hydroxylpropyltrimonium chloride (AquaCat-CG518 (18% AI)) | 0.150 |
| Part 7 | |
| Fragrance | 0.400 |
| Part 8 | |
| Color solution (0.1% solution) | 0.500 |
| DMDM Hydantoin (Glydant from Lonza) | 0.450 |
| Kathon CG (from Rohm & Haas) | 0.070 |
| Water soluble Extract | 0.100 |
| NaCl | +/−1.200 |
| Citric acid (50% solution) | 0.300 |

Comparative Examples A–C

The General Method described above was adapted to make Formulations A–C.

Comparative Formula A is also a conditioning shampoo but is different from the invention in that the Comparative Formula A contains the silicone quaternium-8 and cellulosic quaternary conditioning ingredient in combination with a typical commercially available higher molecular weight guar hydroxypropyl trimonium chloride available from Cognis Inc. This version is substantially higher than the molecular weight range called for in this invention.

Comparative Formula B is also a conditioning shampoo with Silicone Quaternium-8 and cellulosic quaternary conditioning ingredient maintaining the same amount of total quaternized conditioning ingredients in the formula but omitting any cationic guar gum.

Comparative Formula C is also a conditioning shampoo exclusive use of the AquaCat™ CG-518 clear cationic solution and Silicone Quaternium-8 conditioning ingredient maintaining the same amount of total quaternized conditioning ingredients in the formula but with additional low molecular weight quaternary guar gum.

| Component | Weight % |
|---|---|
| Comparative Formula A | |
| Part 1 | |
| Deionized water | q.s. |
| Sodium phosphate monobasic | 0.100 |
| Acrylates copolymer (Aqua SF-1) | 1.500 |
| Ammonium lauryl sulfate | |
| NaOH (50% solution) | 28.571 |

-continued

| Component | Weight % |
|---|---|
| Cocamidopropyl betaine (30%) | 6.000 |
| Silicone Quaternium-8 (100% Al) | 0.500 |
| Part 2 | |
| Deionized water | 15.00 |
| Polyquaternium-10 (100% Al) | 0.150 |
| Part 3 | |
| Deionized water | 10.00 |
| Tetrasodium EDTA-62% | 0.120 |
| Part 4 | |
| Guar hydroxylpropyltrimonium chloride (Cosmedia Guar-Cognis-100% Al) | 0.150 |
| Cocodiethanolamide-90% | 1.300 |
| Fragrance | 0.400 |
| Benzophenone-3 | 0.100 |
| Part 6 | |
| Color solution (0.1%) | 0.500 |
| Formalin | 0.100 |
| Water soluble Extract | 0.150 |
| Comparative Formula Example B | |
| Part 1 | |
| Deionized water | q.s. |
| Sodium phosphate monobasic | 0.100 |
| Acrylates copolymer (Aqua SF-1) | 1.500 |
| Ammonium lauryl sulfate | |
| NaOH (50% solution) | 28.571 |
| Silicone Quaternium-8 (Ultrasil Q-Plus) | 0.500 |
| Cocamidopropyl betaine (30%) | 6.000 |
| Part 2 | |
| Deionized water | 15.00 |
| Polyquaternium-10 | 0.300 |
| Part 3 | |
| Deionized water | 10.00 |
| Tetrasodium EDTA-62% | 0.120 |
| Part 4 | |
| Cocodiethanolamide-90% | 1.300 |
| Fragrance | 0.400 |
| Benzophenone-3 | 0.100 |
| Part 6 | |
| Color solution (0.1%) | 0.500 |
| Formalin | 0.100 |
| Water Soluble Extract | 0.150 |
| Comparative Formula C | |
| Part 1 | |
| Deionized water | q.s. |
| Sodium phosphate monobasic | 0.100 |
| Acrylates copolymer (Aqua SF-1) | 1.500 |
| Ammonium lauryl sulfate | |
| NaOH (50% solution) | 28.571 |
| Cocamidopropyl betaine (30%) | 6.000 |
| Silicone Quaternium-8 (Ultrasil Q-Plus) | 0.500 |
| Part 2 | |
| Deionized water | 10.00 |
| Tetrasodium EDTA-62% | 0.120 |
| Part 3 | |
| Guar hydroxylpropyltrimonium chloride (AquaCat ™ CG518 clear cationic solution) | 3.611 |
| Part 4 | |
| Cocodiethanolamide-90% | 1.300 |
| Fragrance | 0.400 |
| Benzophenone-3 | 0.100 |

-continued

| Component | Weight % |
|---|---|
| Part 5 | |
| Color solution (0.1%) | 0.500 |
| Formalin | 0.100 |
| Water Soluble Extract | 0.150 |

Comparison to Example 1: Physical Appearance—Example 1 of the invention was compared to Comparative Formula Example A, B and C. The composition from Example 1 containing the AquaCat™ CG-518 clear cationic solution (which was optically clear) was in accordance with the invention, while Comparative Formula Example A was found to be very hazy and deemed translucent in appearance (incapable of reading 12-point font through the formula contained in a standard transparent polyethylene shampoo bottle of 4 cm thickness) with the naked eye. Comparative Formula B was found to be optically clear in appearance as expected due to Comparative Formula B not containing any type of cationic guar gum. Comparative Formula Example C was found to be hazy in appearance (incapable of reading 12-point font through the formula contained in a standard transparent polyethylene shampoo bottle of 4 cm thickness) (AquaCat™ CG-518) with the naked eye. This level of the low molecular weight quaternary guar gum in the Comparative Formula Example C is above the level defined in this invention did not maintain the required clarity of the formulation and was deemed unacceptable. Further, Comparative Formula Example C displayed a grainy, mucous-like texture that was also deemed unacceptable aesthetically. No further comparative testing was conducted on Comparative Formula Example C to determine hair conditioning benefits due to the unacceptable appearance.

Comparison to Example 1: Performance—Comparisons were done with Example 1 and Comparative Formula A, and Example 1 and Comparative Example B using paired comparison salon tests for the following attributes to assess overall conditioning attributes of the formulas. To evaluate hair attributes and conditioning properties each test used a salon half-head single session double-blind shampoo testing method. Example 1 of the invention was evaluated versus Comparative Example A. The studies used twenty participants all of whom were female, minimum age 18 with normal to dry hair. Monadic evaluations were performed by a trained, licensed cosmetologist. Examples were evaluated on foam attributes after first and second applications, wet hair attributes and dry hair attributes.

Summary of Results for Formula A

Results of this study showed that Example 1 provide parity level of hair conditioning attributes on both wet and dry hair characteristics vs. Comparative Formula A. In addition, Example 1 of the invention provided an improved foam volume and an overall less coated feel on hair. The following data reflects the means for each attribute. An 1 to 15 Unipolar rating Scale was utilized where 1=not at all evident and 15=extremely evident. Results were analyzed statistically and those qualities marked with an asterisk were found to be better at a 95% confidence level.

|  | Comparative Example A | Example 1 |
|---|---|---|
| Foam Attribute | | |
| First Foam-ease of distribution | 10.60 | 10.90 |
| First Foam-flash foam | 9.10 | 9.73 |
| First Foam-volume | 6.23 | 7.35* |
| First Foam-thickness | 8.70* | 8.13 |
| Second Foam-flash foam | 10.80 | 11.60* |
| Second Foam-volume | 10.50 | 11.50* |
| Second Foam-thickness | 8.18 | 7.78 |
| Wet Hair Attributes | | |
| Ease of snag removal | 4.08 | 4.70 |
| Ease of comb slip | 11.50 | 11.50 |
| Foam generation | 0.30 | 0.18 |
| Coated feel | 2.90 | 2.73 |
| Drag resistance | 4.05 | 3.98 |
| Smooth feel scalp | 14.90 | 14.90 |
| Smooth feel hair ends | 14.50 | 14.50 |
| Dry Hair Attributes | | |
| Ease of snag removal | 13.40 | 12.90 |
| Ease of comb slip | 12.20 | 11.90 |
| Coated feel | 3.43 | 3.08* |
| Drag resistance | 1.38 | 1.55 |
| Smooth feel scalp | 15.00 | 15.00 |
| Smooth feel hair ends | 13.80 | 13.70 |
| Course ends | 0.00 | 0.00 |
| Tackiness | 1.13 | 0.80 |
| Curl hold | 12.40 | 11.50 |

Summary of Results for Formula B

Results of this study showed that Example 1 provided a higher level of wet combability (less drag resistance) hair conditioning attributes on wet hair characteristics vs. Comparative Formula B. Other hair attributes were considered statistical parity for both Example 1 and Comparative Formula B with the exception of a more coated feel displayed by Example 1. In addition, Example 1 of the invention provided an improved foam volume vs. Comparative Formula B.

|  | Comparative Example B | Example 1 |
|---|---|---|
| Foam Attribute | | |
| First Foam-ease of distribution | 10.60 | 10.60 |
| First Foam-flash foam | 9.10 | 9.75* |
| First Foam-volume | 6.23 | 6.35 |
| First Foam-thickness | 8.70 | 8.05 |
| Second Foam-flash foam | 10.80 | 10.90 |
| Second Foam-volume | 10.50 | 11.10* |
| Second Foam-thickness | 8.18 | 8.85 |
| Wet Hair Attributes | | |
| Ease of snag removal | 4.88 | 5.85* |
| Ease of comb slip | 11.50 | 11.60 |
| Foam generation | 0.00 | 0.08 |
| Coated feel | 2.48 | 3.20* |
| Drag resistance | 4.05 | 3.73 |
| Smooth feel scalp | 15.00 | 14.90 |
| Smooth feel hair ends | 14.00 | 14.30 |
| Dry Hair Attributes | | |
| Ease of snag removal | 12.80 | 12.70 |
| Ease of comb slip | 11.90 | 11.50 |
| Coated feel | 2.80 | 3.80* |
| Drag resistance | 1.83 | 1.33* |
| Smooth feel scalp | 15.00 | 14.90 |
| Smooth feel hair ends | 13.10 | 13.60 |
| Course ends | 0.10 | 0.050 |
| Tackiness | 3.23 | 2.53 |
| Curl hold | 11.80 | 11.70 |

The compositions of the invention are substantially and surprisingly better than the prior art composition in numerous hair care properties.

What is claimed is:

1. A conditioning shampoo comprising:
   (a) 8–18 weight % of an anionic surfactant;
   (b) 0.5–0.8 weight % of a conditioning system comprising:
      (i) 0.1–0.75 weight % of a silicone quaternium material which is silicone Quaternium-8;
      (ii) 0.1–0.5 weight % of a low molecular weight guar gum with a molecular weight less than 100,000 centipoise as an aqueous clear cationic solution of a modified polysaccharide clear cationic solution; and
      (iii) 0.1–0.5 weight % of Polyquaternium-10;
   (c) 1.0–6.0 weight % of an amphoteric surfactant;
   (d) 0.5–5.0 weight % of a member selected from the group consisting of cocodiethanol amide, and cocomonoethanol amide; and
   (e) the remainder as water; provided that (1) the viscosity of the shampoo is at least 3500 cps; and (2) if cocodiethanol amide is used with a betaine, a salt is included in an amount of 0.1%–2.00 weight % to obtain a viscosity of at least 3500 cps.

2. A conditioning shampoo according to claim 1 comprising 8–14 weight % of the anionic surfactant.

3. A conditioning shampoo according to claim 1 wherein the low molecular weight guar gum has a molecular weight in the range of 40,000–65,000 cps.

4. A conditioning shampoo according to claim 1 comprising 1–3 weight % of the cocodiethanol amide or cocomonoethanol amide.

5. A conditioning shampoo according to claim 1 comprising (a) 1–3 weight % amphoteric surfactant and further comprising a semi-polar surfactant or from 1–3 weight % of additional nonionic surfactant.

6. A conditioning shampoo according to claim 1 which further comprises silicone-free microsponges.

7. A conditioning shampoo according to claim 1 which is free of both microsponges and stabilizers.

8. A conditioning shampoo according to claim 1 which further comprises stabilizers to control foam aesthetics.

9. A conditioning shampoo according to claim 1 which has a modified viscosity in the range of 500–3000 centipoise.

10. A conditioning shampoo according to claim 1 which has a modified viscosity in the range of 300–2000 centipoise.

11. A conditioning shampoo according to claim 1 which is made as an aerosol foam using a liquid material having a viscosity in the range of 300–2500 centipoise.

12. A conditioning shampoo according to claim 1 wherein the low molecular weight quaternized guar gum comprises guar hydroxypropyltrimonium chloride having a weight average molecular weight between 5,000–200,000 and a light transmittance greater than 80% at a wavelength of 600 nm in a 10% aqueous solution.

13. A conditioning shampoo according to claim 1 wherein the anionic surfactant is selected from the group consisting of C8–18 alkyl sulfates, alkyl ether sulfates, alkaryl sulfonates, alkyl sulfosuccinates, n-alkyl sarcosinates, alkyl phosphates, alkyl ether phosphates, alkyl ether carboxylates and alpha-olefin sulfonates, and ammonium, sodium, magnesium and mono-, di- and triethanolamine salts thereof, wherein the alkyl ether sulfates, alkyl ether phosphates and alkyl ether carboxylates contain from 1 to 10 ethylene oxide units per molecule.

14. A conditioning shampoo according to claim 13 wherein the anionic surfactant is a member selected from the group consisting of sodium lauryl sulfate, sodium laureth sulfate, ammonium lauryl sulfate, ammonium laureth sulfate, disodium laureth sulfosuccinate, disodium ricinoleamido monoethanolamide sulfosuccinate, sodium cocoyl isethionate, sodium methyl oleoyl taurate, sodium methyl cocoyl taurate, sodium laureth-13 carboxylate, sodium C14–16 olefin sulfonate, sodium laureth-4 phosphate, laureth-3 phosphate, triethylanolamine lauryl sulfate, magnesium lauryl sulfate, sodium tridecyl sulfate, and alpha-olefin sulfate.

15. A conditioning shampoo according to claim 13 wherein the anionic surfactant is a member selected from the group consisting of ammonium laureth sulfate, ammonium lauryl sulfosuccinate and triethanolamine lauryl sulfate.

16. A conditioning shampoo according to claim 13 wherein the anionic surfactant is a member selected from the group consisting of sodium lauryl sulfate, triethanolamine lauryl sulfate, sodium lauryl ether sulfate 1 EO, 2EO and 3EO and ammonium lauryl ether sulfate 1EO, 2EO and 3EO.

17. A conditioning shampoo according to claim 1 wherein the amphoteric surfactant is a member selected from the group consisting cocamidopropyl hydroxy sultaine, cocoamphocarboxyglycinates, glycines cocoamidopropyldimethylglycine, sodium lauriminodipropionate, sodium cocamphopropionate, disodium cocoamphodipropionate, cocoamphocarboxypropionate, cocamidopropyl betaine, cocobetaine, and oleamidopropyl betaine.

18. A conditioning shampoo according to claim 3 wherein the nonionic surfactant is a member selected from the group consisting of (a) condensation products of C8–18 aliphatic primary or secondary linear branched chain alcohols with alkylene oxide units selected from the group consisting of ethylene oxide and propylene oxide, and (b) phenols with alkylene oxide units selected from the group consisting of ethylene oxide and propylene oxide, wherein the alkylene oxide units have 6 to 30 alkylene oxide groups.

19. A conditioning shampoo according to claim 3 wherein the nonionic surfactant is a member selected from the group consisting of C10–C18 fatty acid alkanolamides.

20. A conditioning shampoo according to claim 3 wherein the semi-polar surfactant is an amine oxide having a hydrophobic portion wherein the hydrophobic portion of the amine oxide surfactant is a fatty hydrocarbon chain having from about 10–21 carbon atoms.

* * * * *